United States Patent [19]

Sander et al.

[11] Patent Number: 4,895,989
[45] Date of Patent: Jan. 23, 1990

[54] PROCESS FOR PRODUCING ALKALI METAL ALCOHOLATES

[75] Inventors: Ulrich Sander, Friedrichsdorf; Pavel Soukup, Hammersbach; Harald Helmrich, Frankfurt am Main; Wilfried Weiss, Oberursel, all of Fed. Rep. of Germany

[73] Assignee: Metallgesellschaft Aktiengesellschaft, Frankfurt am Main, Fed. Rep. of Germany

[21] Appl. No.: 217,759

[22] Filed: Jul. 11, 1988

[30] Foreign Application Priority Data

Jul. 14, 1987 [DE] Fed. Rep. of Germany ....... 3723193

[51] Int. Cl.$^4$ .................. B01D 13/00; C07C 31/30
[52] U.S. Cl. ..................................... 568/851; 568/916; 55/16; 202/182; 202/197; 203/18; 203/19; 203/39; 203/40; 203/DIG. 6; 203/DIG. 13; 210/490; 210/500.41; 210/500.42; 210/500.43; 210/640
[58] Field of Search ............. 203/89, 99, 98, 40, 203/39, DIG. 16, DIG. 6, 18, 19, DIG. 13; 202/182, 197; 568/851, 916; 210/640, 490, 500.43, 500.41, 500.42; 55/16, 158, 68

[56] References Cited

U.S. PATENT DOCUMENTS

| | | | |
|---|---|---|---|
| 2,877,274 | 3/1959 | Kramis | 568/851 |
| 4,230,463 | 10/1980 | Henis et al. | 55/16 |
| 4,405,409 | 9/1983 | Tusel et al. | 203/39 |
| 4,421,936 | 12/1983 | Smith et al. | 568/851 |
| 4,591,440 | 5/1986 | Higashimura et al. | 210/640 |
| 4,620,900 | 11/1986 | Kimura et al. | 159/DIG. 27 |
| 4,728,431 | 3/1988 | Nagura et al. | 210/640 |
| 4,743,343 | 5/1988 | Sakai | 203/40 |
| 4,755,299 | 7/1988 | Brüschke | 210/640 |

FOREIGN PATENT DOCUMENTS

| | | | |
|---|---|---|---|
| 3526755A1 | 1/1987 | Fed. Rep. of Germany | |
| 135190 | 4/1979 | German Democratic Rep. | 568/851 |
| 58-21629 | 2/1983 | Japan | 568/916 |
| 60-202705 | 10/1985 | Japan | 203/39 |
| WO86/00819 | 2/1986 | World Int. Prop. O. | |

OTHER PUBLICATIONS

Chem Ing Tech 58, 2/(1986) Nr. 9, S. 740–742 VCH Verlagsgesellschaft mbH D-6940 Weinheim, 1986 Konzentrierung Von Ethanol Durch Pervaporation, Jürgen Kaschemekat, Bernnd Barbknecht und Karl W. Böddeker.

*Primary Examiner*—Wilbur Bascomb
*Attorney, Agent, or Firm*—Herbert Dubno; Jonathan Myers

[57] ABSTRACT

A process is described for the production of alcoholates from alkali metal hydroxides and aliphatic alcohol which in their molecule contain 1 to 6 carbon atoms. The alcoholates are produced in that alkali metal hydroxide is mixed with an alcohol and is reacted with said alcohol at a temperature from 80° to 110° C., preferably from 80° to 100° C., and under a pressure from 0.3 to 1.2 bars, the alcohol water mixture which evaporates during the reaction is separated into its components by at least one membrane, the alcohol vapor and the water vapor are condensed and the condensed alcohol is recycled to the reaction.

9 Claims, 1 Drawing Sheet

PROCESS FOR PRODUCING ALKALI METAL ALCOHOLATES

FIELD OF THE INVENTION

Our present invention relates to a process for producing alcoholates from alkali metal hydroxides and an aliphatic alcohol containing 1 to 6 carbon atoms. This means that the raw materials which may be used in the process can be one or more alkali metal hydroxides, namely, LiOH, NaOH, KOH, RbOH and CsOH, and one or more of the aliphatic alcohols, methanol, ethanol, propanol, butanol, pentanol and hexanol and all $C_3$–$C_6$ isomeric alcohols.

BACKGROUND OF THE INVENTION

The production of alkali metal alcoholates in accordance with the equation $$ROH + MeOH \rightleftharpoons ROMe + H_2O,$$

wherein Me=Li, Na, K, Rb, Cs, is accompanied by formation of water, which must be removed from the equilibrium reaction if a substantially quantitative reaction and/or a substantially anhydrous end product are desired.

While the water which has been formed may be removed by distillation, this approach gives rise to difficulties if the water and the alcohol ROH constitute an azeotrope or if the water has an evaporation behavior which is similar to that of the alcohol.

In either case, a water-containing mixture will be evaporated and it is necessary to separate said mixture into its constituents.

That separation often involves technological difficulties and/or considerable costs so that another process is required for a substantially quantitative separation of the water.

OBJECT OF THE INVENTION

It is an object of the invention to provide a process for making an alkali metal alcoholate which can be carried out by using an inexpensive apparatus and permits an almost quantitative and quick separation of the reaction water which is continually formed during the formation of the alcoholate.

SUMMARY OF THE INVENTION

This object is attained, in accordance with the invention, in that an alkali metal hydroxide is mixed with an alcohol and is reacted with said alcohol at a temperature from 50° to 110° C., preferably from 80° to 100° C., and under a pressure from 0.3 to 1.2 bars.

The alcohol-water mixture which evaporates during the reaction is separated into its components by at least one membrane, the alcohol vapor and the water vapor are condensed and the condensed alcohol is recycled to the reaction.

Because the reaction mixture always contains only a relatively small quantity of water and the water must be removed quickly, the water may desirably be entrained by the alcohol which is contained in the reaction mixture and which evaporates during the formation of the alcoholate and promotes the distillation.

We have surprisingly found that the vapor phase which is formed during the formation of the alcoholate can easily and economically be separated into its constituents by pervaporation.

In accordance with the invention, even small proportions of water can be separated from the vapor phase with a high selectivity, i.e., with a high economy, and the process in accordance with the invention affords the advantage that short reaction times are sufficient and high yields are achieved.

While it has already been proposed in U.S. Pat. No. 4,405,409 that mixtures of organic liquids and water should be dewatered in that the water content is decreased initially by distillation and subsequently by pervaporation—i.e., by a separation of mixed vapors by means of a membrane—, it could not have been expected that said procedure can be adopted also in the production of alkali metal alcoholates, because an individual of ordinary skill in the art could not have predicted that the small quantity of water which is contained in a liquid phase during the formation of the alcoholate could be transformed to the vapor phase and could subsequently be removed quantitatively from the vapor phase by pervaporation.

In accordance with the invention it is particularly desirable to mix the alkali metal hydroxide and the alcohol in a molar ratio from 1:2 to 1:10 because that mixing ratio will ensure that the quantity of alcohol which is present will be sufficient throughout the reaction time to entrain the continually formed water as the alcohol is evaporated.

Also in accordance with the invention the membrane comprises a carrier, a porous supporting membrane applied to said carrier, and a non-porous separating layer disposed on the outside of the supporting membrane, wherein the carrier has a thickness from 50 to 300 $\mu$m, the supporting membrane has a thickness from 50 to 500 $\mu$m and the separating layer has a thickness from 0.2 to 0.5 $\mu$m.

Such a membrane has a very high mechanical strength. Regarding resistance to aging and selectively, this membrane will have particularly desirable properties if the carrier consists of a woven or non-woven polyester fabric, the supporting membrane consists of polyacrylonitrile or a polysulfone, the separating layer consists of polyvinylalcohol, and the diameter of the pores in the supporting membrane decreases in the direction from the carrier to the separating layer.

The pores of the supporting membrane have a diameter from 0.05 to 10 $\mu$m where they adjoin the separating layer.

Also in accordance with the invention, a membrane exchange area from 20 to 40 m$^2$, preferably 25 to 35 m$^2$, is utilized per kg of water vapor to be separated per hour, because in that case vapor at a relatively high rate can be separated into its constituents at an adequate rate and with adequate selectivity.

In a particularly desirable embodiment of the process in accordance with the invention the mixed alcohol and water vapors are heated before their separation to a temperature which is up to 50° C. above the temperature of the reaction mixture, but does not exceed 120° C.

In that case the membrane will not be subjected to thermal deterioration and the membrane will always be in contact with a vapor phase which is free of condensate droplets.

Finally, a further feature of the invention resides in that the mixed alcohol and water vapors are caused to flow over a mist collector before their separation. In that case, alcoholate droplets which have been entrained will reliably be removed from the vapor phase so that the life of the membrane will be prolonged.

The alcoholates which have been produced by the process in accordance with the invention have a very high purity if the alkali metal hydroxides are free of oxygen and peroxides, if the alcohols are free of oxygen and of aldehydes and ketones, and if the atmosphere contained in the processing equipment is free of oxygen.

The alkali metal hydroxide content of the alcoholates can further be decreased in that the alcoholates are purified by a recrystallization in which a solvent is used which consists of the alcohol that is also contained in the alkali metal alcoholate. The condensation of the alcohol and water vapors may be effected immediately after the membrane or in a separate condenser. The condensation of the alcohol vapors results in a pressure drop. The reduced pressure may be used to adjust the reaction pressure that is to be maintained during the formation of the alcoholates.

The process in accordance with the invention may be carried out as a discontinuous or continuous process.

In the discontinuous process, the alcohol is evaporated until the desired alcoholate concentration in the reaction mixture has been achieved.

In a continuous process the reaction mixture is passed through a plurality of reactors in which different reaction conditions are maintained so that the alcoholate concentration increases from reactor to reactor.

The last reactor may consist of a spray dryer, in which the residual alcohol is removed from the alcoholate. The alcoholate produced by the process in accordance with the invention are obtained in a very high yield and in a high purity.

BRIEF DESCRIPTION OF THE DRAWING

The above and other objects, features and advantages of our invention will become more readily apparent from the following description, reference being made to the accompanying highly diagrammatic drawing in which.

SPECIFIC DESCRIPTION

Figure 1:
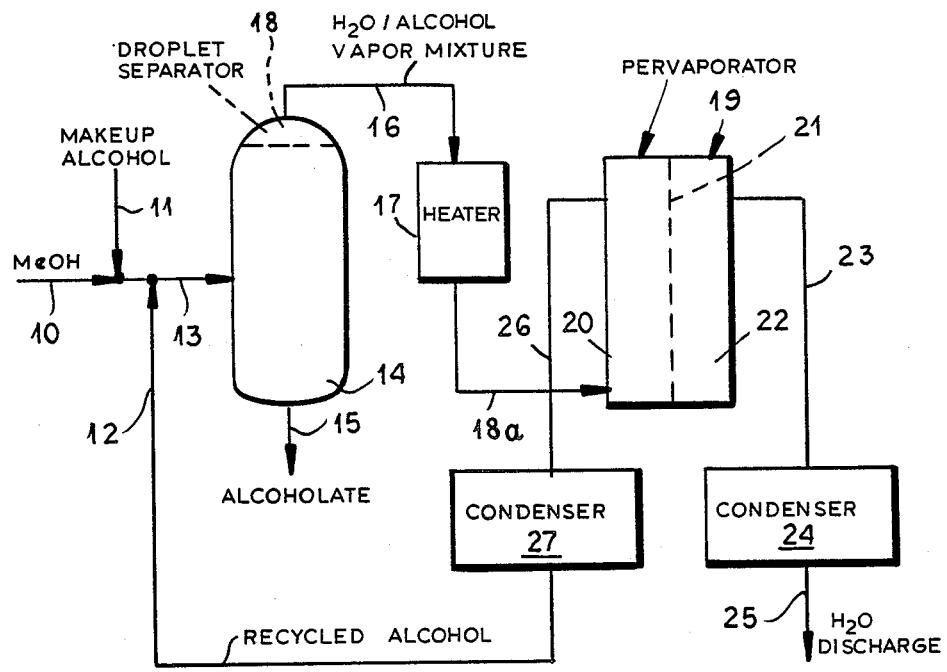
FIG. 1 is a flow diagram illustrating an apparatus for carrying out the method of the invention.

As can be seen from FIG. 1, the alkali hydroxide is supplied at 10 and is combined with a $C_1$-$C_6$ aliphatic alcohol as represented by lines 11 and 12 to form a mixture at 13 fed to a reactor 14. The alkali metal hydroxide reacts with the aliphatic alcohol to form an alcoholate which can be recovered as represented at 15. The reaction is carried out at a temperature of substantially 50° to 110° C. under a pressure of 0.3 to 1.2 bar.

During the reaction a water/alcohol vapor phase mixture is formed which is removed from the reactor at 16 and delivered to a superheater 17. Before leaving the reactor 14, this mixture may pass through a droplet separator or mist collector 18a which can be provided at the upper end of the reactor.

The superheated mixture, at a temperature no greater than 120° C. but up to 50° C. above the reaction temperature in the reactor, is delivered at 18 to a pervaporator unit which can have a multiplicity of cells of which only the single cell 19 has been shown. The cell 19 can comprise a retentate compartment 20 separated by the membrane 21 from a permeate compartment 22. The water vapor which permeates through the membrane 21 is carried off at 23 to a condenser 24 and can be discharged at 25. The retained vapor, namely, the alcohol is fed at 26 to a condenser 27 from which recycled alcohol is withdrawn and is fed at 12 back to the reactor. The makeup alcohol is separated by the line 11. The pervaporator cells and condenser cells may be provided in a plate construction as described, for example, in copending application Ser. No. 07/028,479 filed Mar. 20, 1987 commonly assigned with the present application and now abandoned.

Figure 2:
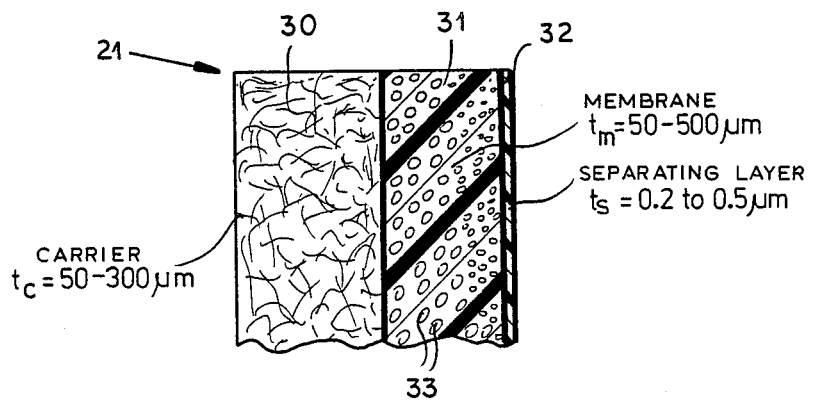
FIG. 2 is a diagrammatic cross sectional view through a portion of the membrane used in FIG. 1.

As can be seen from FIG. 2, the membrane 21 can comprise a woven or nonwoven carrier 30 on which a membrane like layer 31 which is porous is applied. A very thin layer 32 which may be nonporous but can be semipermeable is applied on the outerface of layer 31. As has been shown diagrammatically the pores 33 of layer 31 decrease in pore size from the carrier side of this layer to the separating side thereof.

SPECIFIC EXAMPLE

A reactor was charged with 18 kg KOH and 82 kg $C_2H_5OH$. The KOH has a water content of about 10% by weight and was free of potassium peroxide and oxygen. The ethanol which was used was purged with nitrogen to remove any oxygen before the ethanol was used, and did not contain aldehydes.

Before the reactor was charged with the raw materials, the reactor was purged with nitrogen to remove all oxygen from the reaction space.

The alcoholate was formed over a reaction time of 4 hours at a reaction temperature of about 80° C. and under a reaction pressure of about 0.9 bar. The formation of the alcoholate was accompanied by an evaporation of ethanol and water. The rate of water evaporation decreased during the reaction time.

The mixed ethanol and water vapors were conducted from the reactor to a mist separator, in which the droplets of the reaction mixture which had been entrained as a result of the evaporation were retained.

The vapor phase was then fed to a superheater, which was maintained at a temperature of 100° C. The superheated vapor phase was then fed to a pervaporator, which had a separating membrane surface area of 240 $m^2$. The water vapor contained in the vapor phase passed through the membrane. The ethanol vapor was retained by the membrane and left the pervaporator.

The anhydrous ethanol vapor entered a condenser which the ethanol was liquefied so that a reduced pressure was established, which was used to control the reaction pressure.

The liquid ethanol was supplied to a storage container and was re-used for the production of alcoholate. The water which had been separated by the membrane was condensed and discarded. When the reaction had been terminated, the reactor contained a liquid product which consisted of 19.7% by weight $C_2H_5OK$, 0.7% by weight KOH, balance $C_2H_5OH$. The liquid product was colorless and did not contain organic impurities.

We claim:

1. A process for producing an alkali metal alcoholate, comprising the steps of:
   (a) mixing an alkali metal hydroxide with an alcohol capable of reacting therewith to form an alcoholate and reacting the resulting mixture at a temperature of 50° to 110° C. under a pressure of 0.3 to 1.2 bar to produce an alkali metal alcoholate and a vapor-phase alcohol-water mixture and separating the alkali metal alcoholate from the vapor phase alcohol-water mixture;

(a₁) heating said vapor-phase alcohol-water mixture to a temperature above the reaction temperature in step (a) but less than 120° C. prior to separation of the vapor-phase alcohol-water mixture;

(b) separating the components of said vapor-phase alcohol-water mixture by pervaporation through at least one membrane with one of said components permeating said membrane while the other component is retained thereby to recover alcohol vapor and water vapor from said vapor-phase alcohol-water mixture;

(c) separately condensing the recovered alcohol and water vapors of step (b);

(d) recycling condensed alcohol from step (c) to step (a) for reaction with alkali metal hydroxide; and (e) recovering the alkali metal alcoholate produced in step (a).

2. The process defined in claim 1 wherein said temperature is 80° to 100° C.

3. The process defined in claim 1 wherein said alkali metal hydroxide and said alcohol are mixed in a molar ratio of substantially 1:2 to 1:10.

4. The process defined in claim 1 wherein said membrane comprises a carrier having a thickness of substantially 50 to 300 μm, a porous supporting membrane layer on said carrier and of a thickness of substantially 50 to 500 μm, and a nonporous separating layer on a surface of said porous supporting membrane layer opposite said carrier of a thickness of substantially 0.2 to 0.5 μm.

5. The process defined in claim 4 wherein said carrier is a woven or nonwoven polyester fabric, said porous supporting membrane layer is composed of polyacrylonitrile or polysulfone, the separating layer is composed of polyvinylalcohol, and the pore diameter of pores of said porous supporting membrane layer decreases from the carrier to the separating layer.

6. The process defined in claim 1 wherein said membrane has a membrane exchange area of substantially 20 to 40 m² per kg of water vapor permeating therethrough per hour.

7. The process defined in claim 6 wherein said membrane has a membrane exchange area of substantially 25 to 35 m² per kg of water vapor permeating therethrough per hour.

8. The process defined in claim 1 wherein said vapor-phase alcohol-water mixture is heated to a temperature of at most 50° C. above the reaction temperature in step (a).

9. The process defined in claim 1, further comprising the step of passing said vapor-phase alcohol-water mixture through a droplet separator to remove entrained alcoholate therefrom prior to separation in step (b).

* * * * *